United States Patent
Brahm

(10) Patent No.: US 10,722,539 B2
(45) Date of Patent: Jul. 28, 2020

(54) CADAVERIC DERIVED WOUND TREATMENT AND METHOD OF USE

(71) Applicant: Brahm Holdings, LLC, Germantown, TN (US)

(72) Inventor: Timothy R. Brahm, Germantown, TN (US)

(73) Assignee: Brahm Holdings, LLC, Germantown, TN (US)

( * ) Notice: Subject to any disclaimer, the term of this patent is extended or adjusted under 35 U.S.C. 154(b) by 85 days.

(21) Appl. No.: 15/223,831

(22) Filed: Jul. 29, 2016

(65) Prior Publication Data

US 2017/0027992 A1 Feb. 2, 2017

Related U.S. Application Data

(60) Provisional application No. 62/198,711, filed on Jul. 30, 2015.

(51) Int. Cl.

| | | |
|---|---|---|
| *A61K 35/34* | (2015.01) | |
| *A61K 35/36* | (2015.01) | |
| *A61K 35/35* | (2015.01) | |
| *A61K 9/70* | (2006.01) | |
| *A61K 47/42* | (2017.01) | |
| *A61K 45/06* | (2006.01) | |
| *A61K 35/28* | (2015.01) | |
| *A61K 38/39* | (2006.01) | |
| *A61K 9/00* | (2006.01) | |
| *A61K 45/00* | (2006.01) | |

(52) U.S. Cl.
CPC ............ *A61K 35/34* (2013.01); *A61K 9/0014* (2013.01); *A61K 9/0019* (2013.01); *A61K 9/703* (2013.01); *A61K 35/28* (2013.01); *A61K 35/35* (2013.01); *A61K 35/36* (2013.01); *A61K 38/39* (2013.01); *A61K 45/00* (2013.01); *A61K 45/06* (2013.01); *A61K 47/42* (2013.01)

(58) Field of Classification Search
CPC ........ A61K 35/34; A61K 38/39; A61K 45/00; A61K 9/0019; A61K 45/06; A61K 9/703
See application file for complete search history.

(56) References Cited

U.S. PATENT DOCUMENTS

| | | | | |
|---|---|---|---|---|
| 4,294,860 | A | * 10/1981 | Roth ...................... | A23B 4/064 426/417 |
| 7,131,994 | B2 | * 11/2006 | Mills .................... | A61L 27/3604 623/14.13 |
| 2006/0105017 | A1 | * 5/2006 | Walboomers ........... | A61L 15/18 424/423 |

OTHER PUBLICATIONS

Lavasani et al., 2013, Isolation of Muscle-Derived Stem/Progenitor Cells Based on Adhesion Characteristics to Collagen-Coated Surfaces, Chapter 5, p. 53-65, Stem cells and aging : methods and protocols / edited by Kursad Turksen, Springer protocols, Humana Press ; Springer, c2013).*
Scott et al., J Cachexia Sarcopenis Muscle, 2013, vol. 4, p. 157-169.*
Merriam-Webster online dictionary definition for pad, retrieved on Jun. 23, 2018.*
Encyclopedia of Death and Dying Rigor Mortis and Other Post-mortem Changes—burial, body, life, cause, time, person, human, Putrefaction, 2011, pp. 1/9-9/9, retrieved on Dec. 13, 2018 from deathreference.com/Py-Se/Rigor-Mortis-and-Other-Postmortem-Changes.html.*
Mohan, C., Calbiochem Buffers, 2003, EMD Biosciences Inc. p. 1-32.*

* cited by examiner

*Primary Examiner* — Kade Ariani
(74) *Attorney, Agent, or Firm* — Barnes & Thornburg LLP

(57) ABSTRACT

Wound treatment compositions obtained from cadaveric tissues are provided. Methods of processing such tissues to form wound treatment compositions are provided. Methods of treating a wound are also provided.

12 Claims, No Drawings

CADAVERIC DERIVED WOUND TREATMENT AND METHOD OF USE

CROSS-REFERENCE TO RELATED APPLICATIONS

The present application claims priority to U.S. Provisional Application No. 62/198,711 filed Jul. 30, 2015, the content of which is incorporated herein in its entirety.

FIELD OF THE INVENTION

The present invention is directed to the field of wound treatments, and, more particularly, to wound treatments composed of cadaveric derived components, as well as methods of processing the same to prepare a wound treatment and methods of using the same to treat a wound.

BACKGROUND OF THE INVENTION

Various tissue-based compositions derived from cadaveric donors have been used for many years in various surgical procedures, including treatments for abrasions, lacerations, burns, and other wounds. Various manufacturing processes have also been employed to create wound treatments. There remains a need, however, for unique treatments that exhibit superior efficacy and improved outcomes.

SUMMARY OF THE INVENTION

The present disclosure is generally directed to a wound treatment composition, and processes for producing the wound treatment. The wound treatment composition has unique properties that aid in the healing cascade. The wound treatment composition may be prepared as a viscous formulation that may be applied directly onto or into a wound.

According to one aspect, a wound treatment composition is provided that includes one or more of morselized cadaveric muscle, morselized cadaveric skin, and adipose tissue. According to one embodiment, the muscle tissue is voluntary muscle tissue. According to one embodiment, the wound treatment composition includes at least one stem cells derived from morselized cadaveric muscle, morselized cadaveric skin, adipose tissue, or a combination thereof. According to one embodiment, the muscle tissue is substantially devoid of lactic acid, alcohol, or acetic acid. According to one embodiment, the skin tissue is decellularized. According to one embodiment, the composition has a viscosity of greater than 1 mPas. According to one embodiment, the composition is flowable. According to one embodiment, the composition is formulated as a paste or putty. According to one embodiment, the composition is formulated to be self-shaping. According to one embodiment, the adipose tissue is derived or obtained from a cadaver. According to one embodiment, the wound treatment includes one or more additional components selected from the group consisting of cadaveric stem cells, progenitor cells, cytokines, hormones, germicides, antibiotics, analgesics, local anesthetic agents, biological response modifiers, collagen, and extracellular matrix. According to one embodiment, the composition includes a variety of stem cell types including, but not limited to, pluripotent stem cells, adipose-derived stem cells, muscle stem cells, multipotent stem cells, mesemchymal stem cells, unipotent stem cells, hematopoietic stem cells, and totipotent stem cells. According to one embodiment, the wound treatment includes a collagen source. According to one embodiment, the collagen source is a collagen pad.

According to another aspect, a method of preparing a wound treatment composition is provided that includes the steps of harvesting one or more tissue components from a cadaver donor and morselizing the one or more tissue components to form the wound treatment composition. According to one embodiment, the one or more tissue components is muscle tissue, adipose tissue, or a combination thereof. According to one embodiment, the method further includes the step of adding one or more additional components such as, for example, cytokines, hormones, germicides, antibiotics, analgesics, local anesthetic agents, biological response modifiers, collagen, extracellular matrix, or a combination thereof. According to one embodiment, the method further includes the step of subjecting the one or more tissue components from the cadaver to infectious disease testing at the time of donation or within seven days after donation.

According to another aspect, a method of preparing a wound treatment composition that includes the steps of harvesting one or more tissue components from a cadaver donor, morselizing the one or more tissue components, and extracting one or more stem cells from the tissue component. According to one embodiment, the one or more tissue components is cadaveric muscle, cadaveric tissue, adipose tissue, or a combination thereof. According to one embodiment, the method further includes the step of stimulating at least one stem cell within the one or more tissue components prior to harvesting. According to one embodiment, the method further includes the step of isolating one or more stem cells after extraction.

According to another aspect, a method of treating a wound is provided. The method of treating a wound includes the steps of preparing a wound treatment composition as provided herein and introducing on or around a wound. According to one embodiment, the wound treatment composition includes one or more of morselized cadaveric muscle, morselized cadaveric skin, and adipose tissue. According to one embodiment, the wound includes at least one cut, bruise, burn, ulcer, or lesion, or a combination thereof. According to one embodiment, the step of preparing a wound treatment composition includes the steps of harvesting one or more tissue components from a cadaver donor and morselizing the muscle, skin and adipose tissue to form a viscous composition. According to one embodiment, the adipose tissue is harvested from a cadaver donor. According to one embodiment, the step of introducing the wound treatment composition to the wound includes applying the wound treatment on a surface of the wound. According to one embodiment, the step of introducing the wound treatment to the wound includes injecting the wound treatment into or underneath the wound. According to one embodiment, the method includes a step of introducing a subsequent wound treatment composition to the wound one hour, from one hour to 12 hours, from 12 hours to 24, from 24 hours to seven days, from one week to two weeks, from two weeks to one month, from one month to two months, from two months to six months, from six months to one year, up to one year or combinations thereof, after initial introduction.

According to another aspect, a method of treating or promoting healing of a wound is provided that includes the steps of preparing a wound treatment composition comprising at least one stem cells derived from morselized cadaveric muscle, morselized cadaveric skin, adipose tissue, or a combination thereof and introducing the wound treatment composition to the wound. According to one embodiment, the method further includes the step of adding the at least one stem cells derived from morselized cadaveric muscle, morselized cadaveric skin, adipose tissue, or a combination thereof to a collagen source. According to one embodiment, the collagen source is a collagen pad. According to one embodiment, the morselized cadaveric muscle, morselized cadaveric skin, adipose tissue, or a combination thereof is harvested from a cadaver donor.

DETAILED DESCRIPTION OF THE INVENTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein: rather, these embodiments are provided so that this disclosure will satisfy applicable legal requirements. As used in the specification, and in the appended claims, the singular forms "a", "an", "the", include plural referents unless the context clearly dictates otherwise. As used in the specification, and in the appended claims, the words "optional" or "optionally" mean that the subsequently described event or circumstance can or cannot occur.

As used herein, the term "cadaveric tissue" includes, but is not limited to, muscle, skin, adipose tissue, or a combination thereof, that is obtained or derived from a deceased human corpse or body.

As used to herein, the term "wound treatment composition" refers to a composition that is applied onto, into, or around an injured area of the body.

As used herein, the term "wound" refers to an injured area of the body including, but not limited to, cuts, bruises, burns, ulcers, or lesions. The wound may arise from blunt force trauma, penetrating trauma, gunshot, microbial infection, hypothermia, frostbite, ischemia, tissue hypoxia, microvascular disease, vascular disease, gangrene, sepsis, vasculitis, diabetes mellitis, or other diseases or condition that may cause a wound.

As used herein, "morselization" means to grind up to particle size. Such particles may be uniform in overall shape and size.

As used herein, "adipose tissue" refers to loose connective tissue composed of adipocytes. The adipose tissue may further include adipose-derived stem cells.

As used herein, "flowable" refers to the ability to move along continuously and smoothly such as, for example, in a stream.

The present invention generally relates to a wound treatment composition that is prepared from cadaveric tissue components. In particular, the invention relates to the use of cadaveric tissue to form a wound treatment composition. In a preferred embodiment, the wound treatment composition is substantially aseptic and may either be formulated to form an exterior or surface applied physical barrier or injected into or onto a wound thereby aiding in the healing cascade. In a preferred embodiment, the wound treatment composition is fully resorbed by the body during the healing process. The invention further relates to methods for aseptically processing cadaveric tissue to produce a wound treatment composition.

The wound treatment compositions as provided herein generally aid in promoting healing or regeneration. The wound treatment compositions as provided herein further aid in promoting vascularization in regenerating tissue. The wound treatment compositions as provided herein further aid in promoting growth of a vascular tissue bed. The wound treatment compositions as provided herein further aid in promoting the growth, vascularization, and/or angiogenesis of tissue surrounding the wound.

According to one embodiment, the wound treatment composition includes skin tissue derived from or obtained from a cadaver. According to one embodiment, the skin tissue is decellularized. According to one embodiment, the cadaveric skin is present in an amount of from typically about 0.1% weight of the total wound treatment composition to about 99.9% weight.

According to one embodiment, the wound treatment composition further includes muscle tissue derived from or obtained from a cadaver. According to one embodiment, the muscle tissue is voluntary muscle. According to one embodiment, the muscle tissue is involuntary muscle. According to one embodiment, the muscle tissue is substantially devoid of lactic acid, alcohol, or acetic acid. According to one embodiment, the muscle tissue is present in an amount of from typically about 0.1% weight of the total wound treatment composition to about 99.9% weight.

According to one embodiment, the wound treatment composition further includes adipose tissue. According to one embodiment, the adipose tissue is derived from or obtained from a cadaver. According to one embodiment, the adipose tissue is brown. According to one embodiment, the adipose tissue is white. According to one embodiment, the adipose is removed from beneath cadaveric skin. According to one embodiment, the adipose tissue is removed from around internal cadaveric organs. According to one embodiment, the wound treatment composition further includes a plurality of adipose tissue fragments containing at least one viable adipose-derived stem cell from a cadaveric donor. According to one embodiment, a thrombin source and a fibrinogen source are included in the wound treatment composition to achieve an appropriate gelling or thickening reaction. The adipose tissue aids in filling voids at the site(s) of a wound and enhances the wound healing cascade.

According to certain embodiments, the wound treatment composition includes at least one stem cell extracted and optionally isolated from the skin, muscle or adipose tissue set forth herein. According to one embodiment, the at least one stem cell is added onto or combined with a collagen source as provided herein. According to one embodiment, the at least one stem cell is introduced to a collagen pad. According to one embodiment, the at least one stem cell is introduced to a collagen sheet. According to one embodiment, the at least one stem cell is introduced or otherwise mixed with a collagen source to form a flowable or column formulation.

According to certain embodiments, the wound treatment includes at least one of any type of collagen, including Type I, Type II, and Type III collagens. In one embodiment, a collagen comprises a mixture of collagens, such as a mixture of Type I and Type II collagen. In other embodiments, a collagen is soluble under physiological conditions. Other types of collagen present in musculoskeletal tissues may be employed. Recombinant, synthetic and naturally occurring forms of collagen may be included.

According to certain embodiments, the wound treatment composition includes at least one antimicrobial agent, such as antibiotic, an antiseptic, an antibacterial agent, an iodine-containing agent, a peroxide-containing agent, a silver-containing agent, iodine, povidone-iodine, an iodide ion-containing agent, hydrogen peroxide, a peroxide ion-containing agent, a silver ion-containing agent, or chlorhexadine. In certain embodiments, such an antimicrobial agent is systemically administered to the patient, or such an antimicrobial agent is administered locally at the site of the wound or injury, or in combination with the wound treatment composition. Such an antimicrobial agent may be systemically administered to the patient, administered locally at the site of the wound or injury, or a combination thereof, before, after, or concomitant to performing the introduction of the wound treatment composition and/or a step of retreatment. The antimicrobial agent may be further selected from the group consisting of: mafenide-acetate, penicillin, ampicillin, penicillin G, clindamycin (Cleocin), Ceftriaxone (Rocephin), erythromycin, gentamicin (Garamycin), clindamycin (Cleocin), metronidazole (Flagyl), Ampicillin-sulbactam (Unasyn), ticarcillin-clavulanate potassium (Timentin), piperacillin-tazobactam (Zosyn), nafcillin (Unipen), Imipenem-cilastatin (Primaxin), a β-lactam, a β-lactamase inhibitor, antipseudomonal cephalosporin, ceftazidime (Fortaz), clindamycin, metronidazole, Vancomycin (Vancocin) an aminoglycoside, aztreonam (Azactam), amphotericin B (Abelcet), a third-generation cephalosporin, and combinations thereof.

According to certain embodiments, the wound treatment composition optionally includes at least one biological agent. Alternatively, at least one biological agent may be administered to the subject in need of treatment. The at least one further biological agent may be selected from the group consisting of an albumin, a growth factor, a cytokine, a VEGF, a PDGF, a BMP, insulin-like growth factor I (IGF-I), an insulin-like growth factor II (IGF-II), a transforming growth factor-β1 (TGF-β1), a transforming growth factor-β2 (TGF-β2), a transforming growth factor-α (TGF-α), a bone morphogenetic protein (BMP), a fibroblast growth factor (FGF), an epidermal growth factor (EGF), a fibroblast growth factor, a keratinocyte growth factor, PDGF-AB, PDGF-AA, PDGF-CC, PDGF-DD, an osteogenin, a protease inhibitor, a metalloproteinase inhibitor, a metalloproteinase-3 inhibitor, ethylenediaminetetraacetic acid (EDTA), ethylene glycol-bis(beta-aminoethylether)-N, N,N',N'-tetraacetic acid (EGTA), aprotinin, and ε-aminocaproic acid (EACA).

According to certain embodiments, the wound treatment composition optionally includes at least one pharmaceutically acceptable liquid that may function as a buffer solution. In some embodiments, the buffer solution comprises a carbonate, a phosphate, phosphate buffered saline, histidine, an acetate, sodium acetate, acetic acid, hydrochloric acid, an organic buffer, lysine, a Tris buffer, tris(hydroxymethyl) aminoethane), N-2-hydroxyethylpiperazine-N'-2-ethanesulfonic acid (HEPES), or 3-(N-morpholino) propanesulfonic acid (MOPS).

According to certain embodiments, the wound treatment composition optionally includes various additional natural or synthetic components (non-naturally occurring) such as proteins, polysaccharides, nucleic acids, carboyhydrates, or synthetic polymers, or mixtures thereof. Non-limiting examples of suitable components include: elastins, polysaccharides, nucleic acids, carbohydrates, proteins, polyurethanes, siloxanes, polysiloxanes, collagens, glycosaminoglycans, oxidized regenerated cellulose (ORO), ethylene diamine tetraacetic acid (EDTA), a poly(lactic-co-glycolitic acid (PLGA), carboxymethylcellulose, granulated collagen-glycosaminoglycan composites, methylcelluloses, hydroxypropyl methylcellulose, hydroxyethyl cellulose alginic acid, poly(a-hydroxy acids), poly(lactones), poly(amino acids), poly(anhydrides), poly(orthoesters), poly(anhydride-co-imides), poly(orthocarbonates), poly(α-hydroxy alkanoates), poly(dioxanones), poly(phosphoesters), poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactide-co-trimethylene carbonate), polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethyl methacrylate, carbon fibers, poly(ethylene glycol), poly(ethylene oxide), polyvinyl alcohol), poly(vinylpyrrolidone), poly(ethyloxazoline), poly(ethylene oxide)-co-poly(propylene oxide) block copolymers, poly(ethylene terephthalate) polyamidearabic gums, guar gums, xantham gums, gelatins, chitin, chitosan, chitosan acetate, chitosan lactate, chondroitin sulfate, N,O-carboxymethyl chitosan, dextrans, fibrin glue, glycerol, hyaluronic acid, sodium hyaluronate, celluloses, glucosamines, proteoglycans, starches, lactic acid, pluronics, sodium glycerophosphate, glycogens, keratins, or any combination thereof.

The cadaveric tissue giving rise to the wound treatment composition as described herein may be produced by processing cadaveric tissue according to the steps provided herein. Processing does not change the physical properties of the resulting treatment so as to yield the cadaveric tissue unacceptable for clinical use. Instruments, solutions, and supplies coming into contact with tissue during the processing of the placental tissue are sterile. All surfaces coming in contact with tissue intended for transplant are either sterile or draped using aseptic technique.

To prepare the wound treatment as provided herein, skin, muscle and adipose tissue is preferably recovered from healthy, adult cadaver. According to one embodiment, the cadaveric tissue is collected and tested as provided herein within seven days after death. According to one embodiment, stem cell growth within the target skin, muscle or adipose tissue is stimulated in the donor prior to death of the donor. According to one embodiment, the stimulation maximizes the harvesting of stem cells from skin, muscle or adipose tissue upon impending death. According to one embodiment, the at least one stem cell is stimulated by needle fracturing the target skin, muscle or adipose tissue.

A comprehensive medical history and behavior risk assessment is obtained from the donor's prior medical records and reviewed prior to donation as per U.S. Public Health Service guidelines. A physical assessment of the cadaveric donor includes at least a limited autopsy, or a recent antemortem or postmortem physical examination. Records or other information received from any source pertaining to risk factors for relevant communicable disease should be reviewed (e.g., social behavior, clinical signs and symptoms of relevant communicable disease, and treatments related to medical conditions suggestive of risk for relevant communicable disease). Examples of these records include: medical examiner reports, police records, and information from other tissue or medical establishments, if applicable.

Infectious disease testing of donor blood specimens is performed for each tissue donor on a specimen collected at the time of donation or within seven days prior to or after donation. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc—total, meaning IgG and IgM); antibodies to the hepatitis C virus (anti-HCV); NAT for HCV; antibodies to human T-lymphotropic virus type I and type II (anti-HTLV-I and anti-HTLV-II); and syphilis (a non-treponemal or treponemal-specific assay may be performed).

The cadaveric tissue as provided herein may be treated with one or more of a variety of antibiotics, cleaned, debrided, and treated with various enzymes. According to one embodiment, the cadaveric skin is decellularized prior to incorporation into the wound treatment composition as provided herein to reduce rejection by the recipient. According to one embodiment, the dermis may be removed for further processing while the epidermis and hypodermis are discarded. The cadaveric muscle tissue as provided herein may be processed in a relaxed or rigor mortis condition. The muscle tissue may be processed to remove lactic acid, alcohol, or acetic acid that may be present. According to one embodiment, the muscle tissue is ground by mechanical means to particulate form and then mixed with sterile water, a 10% glycerol by volume, a saline solution or another biocompatible fluid such as Ringer's solution prior to incorporation into the wound treatment composition.

According to one embodiment, the cadaveric tissue as provided herein may then be morselized individually then mixed together to form a viscous composition. According to one embodiment, the cadaveric tissue as provided herein may be morselized together in a single mixture. According to one embodiment, the cadaveric tissue as provided herein may be morselized in a batch or continuous process. Tissue morselization results in a viscous wound treatment composition. According to one embodiment, the cadaveric tissue as provided herein may be cryopreserved prior to morselization. According to a particular embodiment, the cadaveric tissue as provided herein is cryogenically milled in a CryoMill® (available from Retsch) for one or more cycles. Tissue morselization may occur by any art-recognized method of tissue disruption, including, but not limited to: milling, blending, sonicating, homogenizing, micronizing, pulverizing, macerating, or a combination thereof. According to one embodiment, morselization results in wound treatment composition particles that are typically between 1 μm and 2 mm. According to one embodiment, one or more of the additional wound treatment composition components as provided herein may be added or introduced to the wound treatment composition prior to morselization.

According to one embodiment, the wound treatment composition may be terminally sterilized using irradiation, packaged, and preserved until use. The sterilized wound treatment composition may be stored in any container suitable for long-term storage. Preferably, the sterilized wound treatment is stored in a sterile syringe or cannula until use. According to one embodiment, the wound treatment composition may be cryopreserved and stored until use. According to one embodiment, the wound treatment composition is cryopreserved in liquid nitrogen, glycerol, DMSO, or a combination thereof.

According to one embodiment, a kit is provided. The kit includes at least one wound treatment composition as provided herein. According to one embodiment, the kit may include at least one wound treatment composition in a sterile package. According to one embodiment, the kit may include at least one wound treatment composition within a sterile syringe or cannula. According to one embodiment, the syringe or cannula is ready for use by a medical professional upon receipt. According to one embodiment, the kit may include at least one set of directions for use of the wound treatment composition. According to one embodiment, the kit may further include a collagen source such as, for example, a collagen pad.

According to certain embodiments, the wound treatment composition may be produced in the form of a paste, putty, or other gelatinous formulation. According to one embodiment, the wound treatment composition is moldable. According to one embodiment, the wound treatment composition is semi-solid. According to one embodiment, the wound treatment composition is extrudable. According to one embodiment, the wound treatment composition is shape-retaining. According to one embodiment, the wound treatment composition is flowable. According to a preferred embodiment, the wound treatment composition is formulated to be applied onto, into, or around a wound. According to one embodiment, the wound treatment composition has a viscosity of greater than typically about 1 mPas, 5 mPas, or 10 mPas as determined by ASTM D445. According to a particular embodiment, the wound treatment is injectable by syringe and needle, cannula, or other suitable medical instrument. According to one embodiment, the wound treatment is bioresorbable and may be fully resorbed by the human body.

A method of treating a wound is also provided. According to one embodiment, a wound treatment composition is prepared according to one of the methods as provided herein. According to one embodiment, a wound treatment composition as provided herein is introduced to a wound. According to one embodiment, the wound treatment composition is placed on or around a wound. According to one embodiment, the wound treatment composition is injected into the wound. Modes of administration may include, but not be limited to: intramuscular, subcutaneous, intraperitoneal, percutaneous, soft tissue injection, surgical placement, arthroscopic placement, intravenous, intravascular, intracerebral, transdermal, topical or mucosal. Most preferred methods result in localized administration of the wound treatment to the site or sites of the wound.

According to certain embodiments, a subsequent wound treatment composition may be applied to or injected into the wound one hour, from one hour to 12 hours, from 12 hours to 24, from 24 hours to seven days, from one week to two weeks, from two weeks to one month, from one month to two months, from two months to six months, from six months to one year, up to one year or combinations thereof, after performing the initial introduction step. In certain embodiments, such a subsequent composition is applied to or injected into the wound approximately one week after performing the initial applying step. In certain embodiments, one or more subsequent such wound treatment compositions are periodically applied to the wound. Additionally, the intervals between such periodic applications of such wound treatments may be any interval ranging from approximately 12 hours to approximately 180 days, and preferably at an interval of approximately 3, 5, 7, 10, 14, 15, 21, 28, 30, 60, 90 or 180 days, or any combinations thereof. The intervals between applications may or may not be equal intervals, and may be shorter during the earlier phases of the treatment. The periodic applications of subsequent wound treatment compositions may be applied over a period ranging from approximately one day to approximately one year, and preferably over a period of at least approximately one week, at least approximately one month, at least approximately two months, at least approximately three months, at least approximately four months, at least approximately five months, at least approximately six months, at least approximately nine months, or at least approximately one year after initial introduction step is performed.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

I claim:

1. A wound treatment composition comprising:
   cadaveric muscle particles substantially devoid of lactic acid, alcohol, or acetic acid, the cadaveric muscle particles having a size of from 1 µm to 2 mm; and
   a pharmaceutically acceptable liquid comprising lysine,
   wherein the wound treatment composition is formulated to be self-shaping,
   wherein the wound treatment composition has a viscosity greater than 1 mPas but less than 10 mPas as determined by ASTM D445.

2. The wound treatment composition of claim 1, wherein the composition is flowable.

3. The wound treatment composition of claim 1, wherein the composition is formulated as a paste or putty.

4. The wound treatment composition of claim 1, wherein the wound treatment further comprises cadaveric stem cells, cadaveric cytokines, cadaveric hormones, cadaveric biological response modifiers, cadaveric collagen, cadaveric extracellular matrix, or any combination thereof.

5. The wound treatment of claim 1, further comprising a collagen source.

6. The wound treatment of claim 5, wherein the collagen source is a collagen pad.

7. The wound treatment composition of claim 1, wherein the muscle tissue is voluntary muscle tissue.

8. The wound treatment composition of claim 1, wherein the wound treatment further comprises one or more germicides, antibiotics, analgesics, local anesthetic agents.

9. The wound treatment composition of claim 1, wherein the pharmaceutically acceptable liquid further comprises tris(hydroxymethyl)aminomethane).

10. The wound treatment composition of claim 1, wherein the pharmaceutically acceptable liquid further comprises N-2-hydroxyethylpiperazine-N'-2-ethanesulfonic acid (HEPES).

11. The wound treatment composition of claim 1, wherein the pharmaceutically acceptable liquid further comprises 3-(N-morpholino) propanesulfonic acid (MOPS).

12. The wound treatment composition of claim 1, wherein the pharmaceutically acceptable liquid further comprises sodium acetate.

* * * * *